United States Patent
Hoover

[11] Patent Number: 5,863,289
[45] Date of Patent: Jan. 26, 1999

[54] CROSS-SPIKE PREVENTION SYSTEM

[76] Inventor: Bryan Jay Hoover, 4636 Baverton Dr., Knoxville, Tenn. 37921

[21] Appl. No.: 421,217

[22] Filed: Apr. 13, 1995

Related U.S. Application Data

[62] Division of Ser. No. 117,729, Sep. 7, 1993, Pat. No. 5,439,460.

[51] Int. Cl.⁶ ..................................................... A61B 19/00
[52] U.S. Cl. .............................. 604/410; 604/403; 604/4; 604/905
[58] Field of Search .......................... 604/4–6, 131–133, 604/174–178, 322, 326, 403–404, 408–409, 410, 905; 128/912, 898, DIG. 6, DIG. 12, DIG. 13, DIG. 24, DIG. 26; 222/55, 93–94, 97, 105

[56] References Cited

U.S. PATENT DOCUMENTS

| | | | |
|---|---|---|---|
| 3,625,212 | 12/1971 | Rosenberg | 604/6 |
| 4,150,673 | 4/1979 | Watt | 604/408 |
| 4,443,220 | 4/1984 | Haver et al. | 604/4 |
| 4,637,813 | 1/1987 | De Vries | 604/6 |

Primary Examiner—P. Zuttarelli
Attorney, Agent, or Firm—M. Alex Brown, Patent Attorney

[57] ABSTRACT

An improved device and process of assuring separation of an anticoagulant type fluid from a saline type fluid each of which is utilized in the process and operation of a plasmapheresis apparatus or the process of collecting donor blood, is disclosed. The improvement includes a cross-spike prevention receptacle which is dimensioned, and installed positionally in reference to a plasmapheresis or blood donor apparatus, to receive an anticoagulant fluid container to which a proper respective supply communication line will connect, and to exclude and not receive a saline fluid container or container holding a similar type of fluid, whose fluid line will not reach and connect to the installed cross-spike prevention receptacle. As a part of the process and concepts of the invention the supply containers or bags of fluids which are supplied for use with the invention are provided so that the respective anticoagulant bags are smaller in volume capacity and size than the respective saline solution container bags used in the plasmapheresis or blood collection process, and the bags are dimensioned so that the saline container or bag will not fit into the cross-spike prevention receptacle even upon substantial forcing or where such force would cause rupture of the container or would otherwise result in a container in a condition which could not be reasonably used with respect to the plasmapheresis or blood collection process.

13 Claims, 9 Drawing Sheets

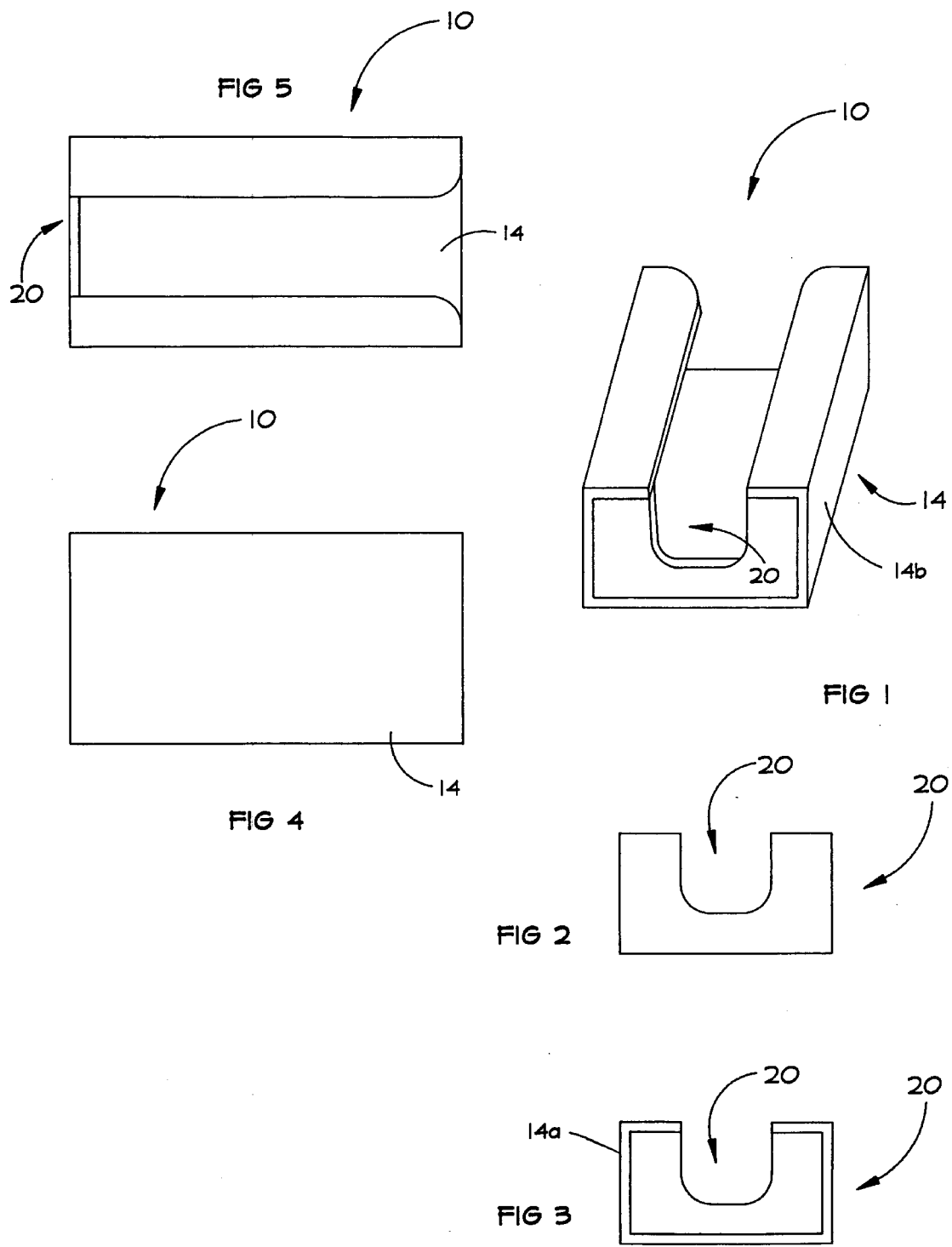

CROSS-SPIKE PREVENTION SYSTEM

This application is a division of application Ser. No. 08/117,729, filed Sep. 7, 1993 U.S. Pat. No. 5,439,460 issued Aug. 8,1995.

BACKGROUND OF THE INVENTION

1. Field of the Invention

This invention relates to an improved device and process for preventing cross-spike or improper substitution or intermixing of critically distinct fluids utilized in connection with a plasmapheresis or blood donor/collection apparatus.

2. Background Information

Typical of the prior art references regarding plasmapheresis and blood donor or collection apparatus or processes are U.S. Pat. Nos. 4.976,851; 4,954,128; 4,043,501; Des. 305, 506; 5,173,257; 5,171,432; 5,171,430; 5,153,828; 5,149, 501; 5.143,602; 5,046,608; 5,037,549; 5,011,705; 4,994, 022; 4,994,021; 4.990,132; 4,975,186; 4,967,763; 4,940, 543; 4,790,330; 4,568,345; 4,044,983; Des. 334,536 and Des. 335,450; which were located during the process of a patent search. Copies or Patent Gazette reference copies of all patents cited were enclosed with the files, sections 1.97–1.99.

U.S. Pat. No. 4,043,501; issued to Larrabee et al; discloses a portable liquid package container for use with a blood washing device, in providing a portable liquid package container arrangement in connective bin-type slots for supplying saline solutions and recovery of washed blood and waste liquid, essentially claiming a linearly oriented, vertically partitioned support area for receiving some five or so collapseable containers for apparent separation and use in the blood washing device. As disclosed and claimed, Larrabee is considerably different in structure and function form the present invention, and would appear by virtue thereof to lend itself to problems of intermixing or substituting improper containers in respective slots.

U.S. Pat. No. 4,976,851; issued to Tanokura et al., disclosing a liquid separator for use as a blood component separator functions to separate a blood component such as blood plasma from centrifugally separated component layers in a flexible blood bag.

U.S. Pat. No. 4,954,128; issued to Ford, discloses a plasmapheresis instrument and a harness set to be utilized therewith. During the infusion cycle, or cycle in which fluids are provided to a respective donor, which alternates with the collection cycle of the Ford device, the blood constituent from the reservoir and a replacement fluid are mixed externally of a reservoir and pumped to the donor. An anticoagulent supply container 44 in Ford, and a replacement fluid supply container 46 therein are essentially provided overhead of the device and oriented in position and relation to the Ford device and its tubing components such that a substantial risk exists for intermixing, improper substitution or cross-spiking of anticoagulent and replacement fluid which during the plasmapheresis process could cause severe damage or death to a respective blood or plasma donor.

Additionally some designs for plasma containers, bottles or the like have been patented such as the above referenced '506 Sittig. '536 Long et al. and the '450 Pezzoli et al. design patent references; but each is substantially different in design from the present invention.

None of the references specifically illustrates the present invention. Nor is the present invention obvious in view of any of the prior art references listed herein. In addition, all of the relevant prior art heretofore known suffer from a number of disadvantages.

(a) The prior art devices do not provide substantially adequate means of preventing against the cross-spiking or cross-connecting of one of several critical fluid lines which may be a part of or necessary in an electrophoresis, plasmaphoresis or blood collection process, such as connection lines from saline solution and anticoagulant fluid.

(b) The prior art devices substantially run the risk of the potentially fatal cross-spiking or cross connecting of anticoagulent fluid and saline solution, where these fluids are incorrectly and improperly provided respectively to a plasma or blood collection device, or device for plasmapheresis, and administered to a plasma or blood donor, causing serious problems for the donor, cell damage or loss to blood already circulating in the plasma-pheresis device, or health problems related to the rapid infusion in the donor of anticoagulant fluid.

(c) It is a further disadvantage of the prior art that required fluids which must be kept separated and utilized in the process of collecting plasma or blood at the right time and location are often provided in linear arrangement, one adjoining the other in position, such that improper storing separation and categorization for proper utilization and safety is frequently subject to occur, resulting in the wrong type of fluid communication lines being connected to an otherwise properly installed fluid container; in each event causing cross-spiking or cross connecting and supply of these critical respective fluids.

(d) Additionally, the prior art devices have not advantageously utilized the size of fluid containers, the length of respective fluid supply lines, proper line guiding means and the spatial location and installation of fluid retaining and holding devices to substantially protect against the danger of crossspiking of critical, independent fluids.

(e) A further disadvantage of the prior art has been that some of the prior art devices or systems provide placement of necessary critical fluids in positions separate from or not integrally related to the central plasmapheresis or blood collection device.

These and other disadvantages of the prior art will become apparent in reviewing the remainder of the present specification and the drawings.

Accordingly, it is an object of the present invention to provide a substantially improved means of assuring separation of important or necessary, respective process and replacement fluids utilized in the operation of a plasma or blood donation-collection device.

It is a further object of the invention to provide a cross-spike prevention system which will substantially prevent cross-mixing of potentially dangerous fluids, physical damage to a respective donor and damage or loss of respective blood cells or materials already in a device for collecting plasma or blood.

It is yet a further object of the present invention to provide a device and system for prevention of cross-spiking or cross-mixing of otherwise potentially dangerous, critical required infusion and collection fluids, which takes advantage of spatial installation and location, tube communication line length and orientation, and strategically placed guide means such that a respective fluid can be properly placed and connected in a cross-spike prevention receptacle which is properly dimensioned to receive only a container of this respective fluid, and which can be attached in a user-friendly manner to a number of plasma and blood collection units as an attached or integral part of a given such unit.

And it is a further object of the present invention to provide a device and system which will improve and make more safe the function and process of many different types of already existing plasmapheresis and blood collection and donor assemblies and apparatus, by improving each respective unit's ability to isolate important fluids to be utilized in a given collection process such that each respective fluid can be utilized in the proper sequence or time to allow the respective device to function properly in preserving collected blood materials and in preventing the infusion of dangerous fluids into a given subject donor.

SUMMARY OF THE INVENTION

The foregoing and other objects of the invention can be achieved with the present invention device, assembly and system which is the improvement of a cross-spike prevention container which is dimensioned to receive a fluid which an operator or person desires to keep separate from other fluids in the operation of a blood or plasma collection apparatus or the like; and where the desired, segregated, separated fluid to be placed in the cross-spike prevention receptacle is provided in a substantially smaller size or volume than another respective fluid from which the desired fluid is to be kept separate. The cross-spike prevention is installed positionally on a collection device, in relation to respective supply tubes for respective fluids so that the proper tube to the desired, segregated fluid installed in the cross-spike prevention container can be guided to and reach the invention receptacle, but supply lines for other fluids cannot reach this container of the present invention.

BRIEF DESCRIPTION OF THE DRAWINGS

FIG. 1 is a bottom perspective view of a preferred embodiment of the novel cross-spike prevention receptacle.

FIG. 2 is a bottom view of a preferred embodiment of the present invention.

FIG. 3 is a top view of the invention.

FIG. 4 is a back view of the invention.

FIG. 5 is a front view of the invention.

REFERENCE NUMERALS IN DRAWINGS

Figure 6:
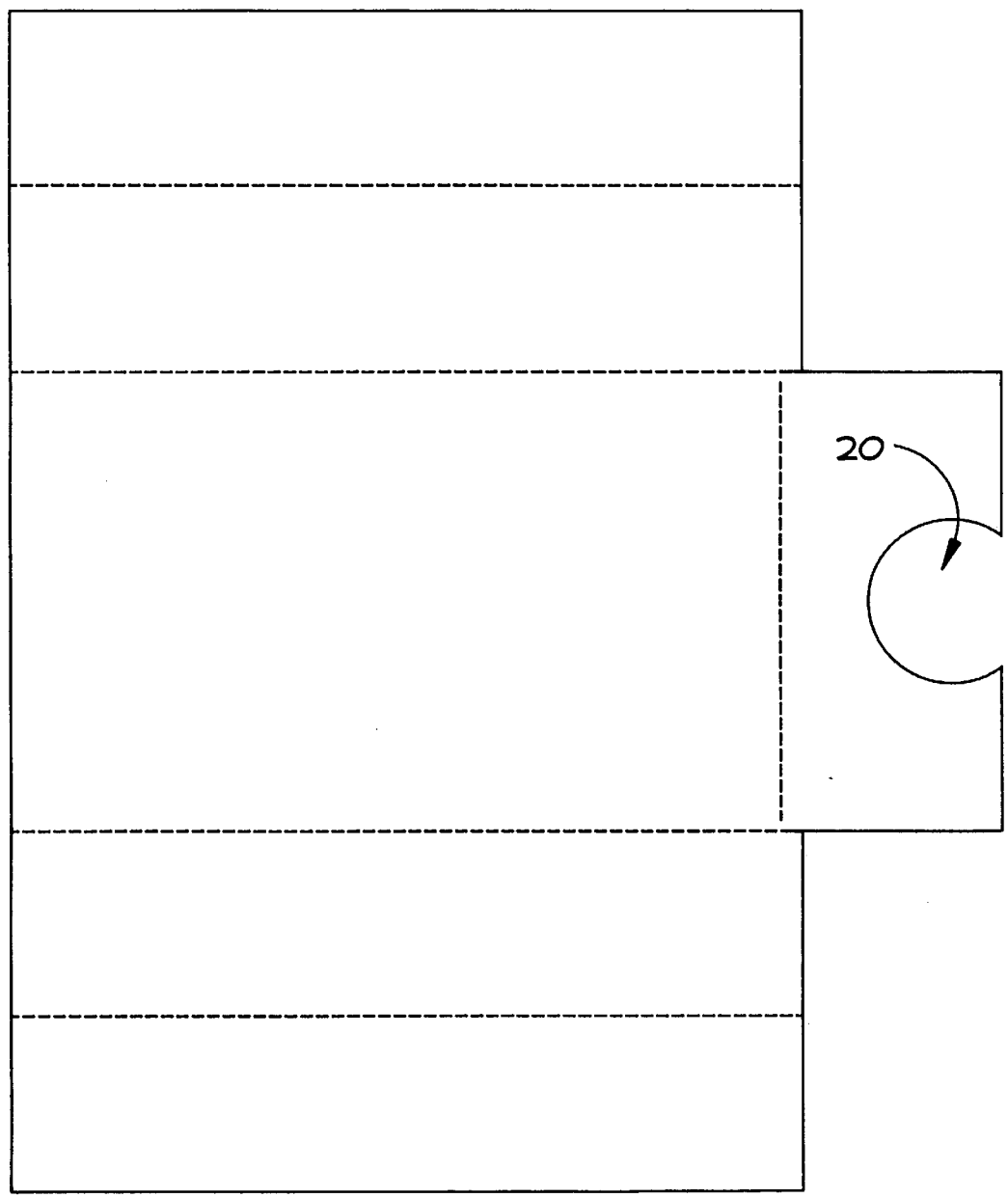
FIG. 6 is a substantially flat layout pattern view of the inside surface of a preferred embodiment of the invention, indicating areas of folding, melting or molding/bending at portions indicated with dotted lines therein.
Figure 7:
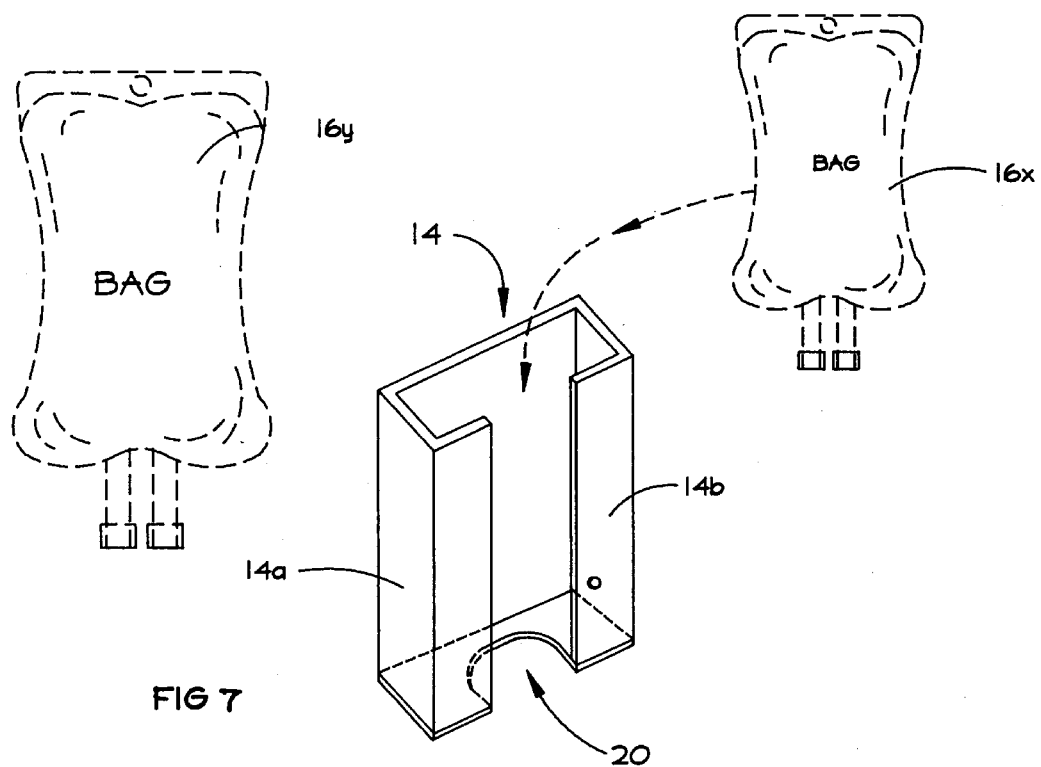
FIG. 7 is an elevated side perspective view indicating proportionate relative sizes of fluid bags utilized with the process of the present invention.

10 cross-spike prevention system
14 receptacle member
14a left side of (14)
16b right side of (14)
16x smaller received fluid container
16y larger rejected fluid container
18 plasmapheresis unit
20 slot (slotted area-extending bottom and length of (14))
22 guide means or system
26 fluid supply line of blood unit
30 cross-spike prevention assembly (preferred embodiment)
34 anticoagulant fluid
38 saline solution
42 plasmapheresis apparatus
46 cross-spike receptacle component
46 anticoagulant fluid supply line
48 saline solution communication line
52 circumferential wall (circular wall) of (30)
54 first open end of (52)
56 second open end of (52)
58 slotted, channeled area of (52)
58a perimeter of slot (58)-first
58b perimeter of slot (58)-second
64 bag support member
66 U-shaped slot of (64)
66a top end portion of (66)
66b top end portion of (66)
68 mount base subassembly
68a attachment means or strip
70 guide means
70a first guide member (70)
70b second guide member (70)
x anticoagulent fluid or like fluid
y saline solution or like fluid
x' supply channel(s) to anticoagulent or like fluid bag
68a adhesive strip (or other attachment or coupling means)

DETAILED DESCRIPTION OF THE PREFERRED EMBODIMENTS OF THE INVENTION

The following description of the preferred embodiments of the concepts of this invention is made in reference to the accompanying figures. Where an individual structural element is depicted in more than one figure, it is assigned a common reference numeral, numeral and prime mark or numeral and small letter for simplification of identification and understanding. Exceptions to this rule of application in preparing the specification herein are set forth with respect to the related embodiments preferred in the invention as to the receptacle member 14 and the cross-spike receptacle component 44, and the various use and explanation of the various fluid containers which can be utilized with the invention, and for which the invention is designed for use with in assuring seperation therebetween. Examples of such designation include the character symbols 16*x*, 16*y*, 34, 38, *x* and *y*. Additionally various plasmapheresis machines, units and systems for which the present invention is designed to be used with have been referenced with regard to the preferred embodiments of the invention as 18 and 42.

Referring now to the drawings, and more particularly to FIGS. 1 through 8, thereof, there is shown a cross-spike, cross-mixing prevention system assembly 10, which is constructed in accordance with the invention to assure and promote the separation of various different types and kinds of process and replacement fluids utilized in the operation and process of a blood donation or other type of blood or blood plasma collection device, apparatus, system or process.

Packages or bags, or fluid container housing fluids to be utilized in plasmapheresis or blood collection units can be provided in different sizes or volumes. In the present invention, it is preferred to provide an anticoagulent fluid container in a bag containing about 250 ml. (milliliters) of anticoagulent; and to provide a saline solution container in a bag containing about 500 ml. of this solution.

The assembly 10 is provided with a receptacle member 14 which in a preferred embodiment is provided with approximate rectangular dimensions of about a length of 6 5/16 in. (inches), or about 15.9 cm. (centimeters); a width of about 1 7/8 in., or about 4.7 cm.; and a length of base of about 3.5 in., or about 9 cm. In so doing, the receptacle 14 is dimensioned so that it will receive a fluid bag 16*x* of about 250 ml. of anticoagulent fluid, generally having a length of about 6 5/8 in or about 16 cm. and an average circumferential-like or elliptical perimeter of about 8 5/8 in. or about 12 to 13 cm. At the stated dimensions, the receptacle will not properly receive, or receive without considerable forcing and/or breakage, a saline solution container-bag 16*y* having about 500 ml. of this solution as its contents, and approximate dimensions of a length of about 7 1/4 in. or about 19 cm. and an approximate circumferential or elliptical perimeter of about 11 in. or about 27 to about 28 cm.

It will be understood that many other types of fluid for use in blood or plasma collection systems can be provided in containers at the stated dimensions or at appropriate ratios in accordance therewith so that the receptacle 14 will act to accept one container 16*x* and reject the other 16*y* for purposes of identification and separation as each respective fluid is utilized in connection with a plasmapheresis device or blood collection unit.

Additionally, in the example of a use of the present invention as heretofore set forth, 250 ml. containers 16*x* of "Anticoagulant Sodium Citrate solution" are utilized, and 500 ml. containers 16*y* of 0.9% Sodium Chloride are utilized. It will be understood that many other pairs of fluids which should not be intermixed could be assured of better separation and prevention of intermixing in many related processes and devices, for, among many others, plasmapherisis, cytapheresis, leukapheresis, thrombocytapheresis and the like, or others.

Figure 8:
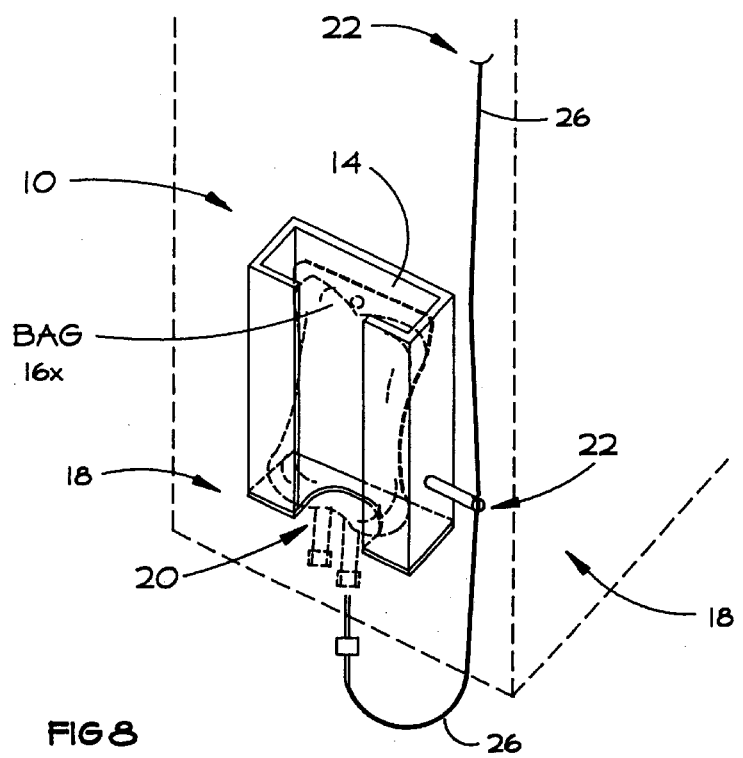
FIG. 8 is a side perspective view of the present invention illustrating the invention installed on a plasmapheresis or blood collection apparatus indicated in phantom lines.
Figure 10:
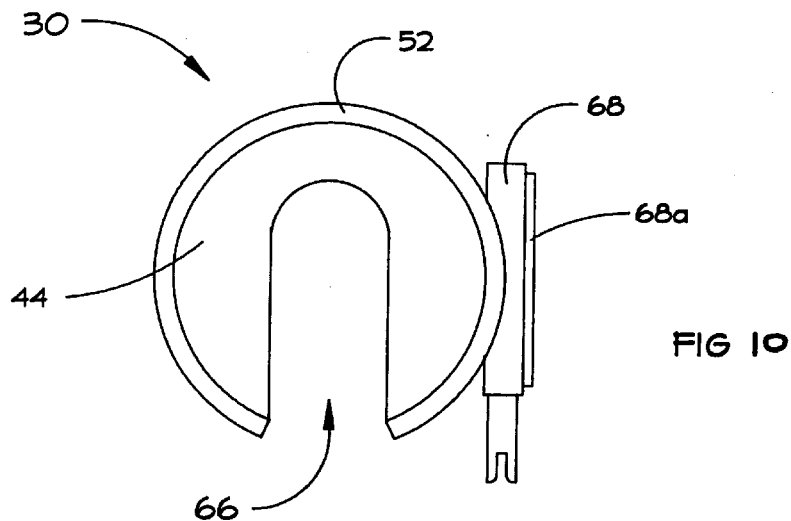
FIG. 10 is a top view of the embodiment illustrated in FIG. 9.
Figure 9:
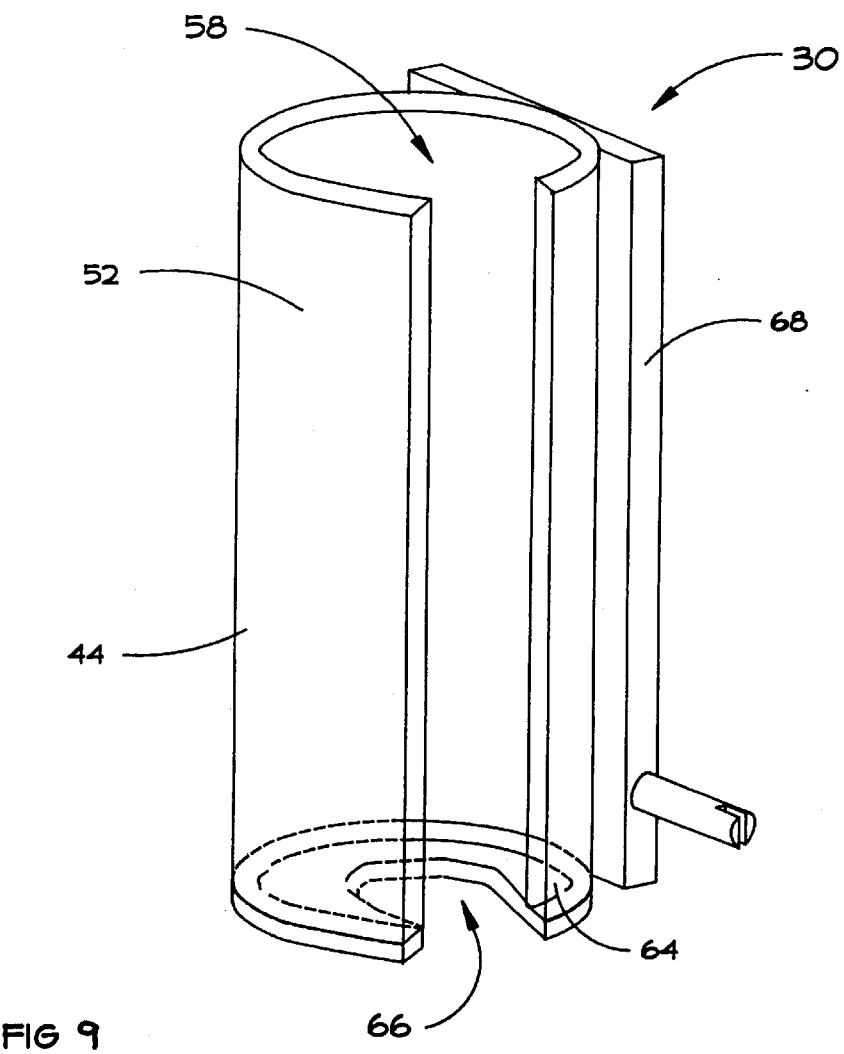
FIG. 9 is a side perspective view of another preferred embodiment of the present invention.

Additionally, the cross-spike prevention system is designed in accordance with the invention to be positioned on and attached to the side or other appropriate location of a plasmapheresis, blood collection or like unit 18 for utilization in facilitating and assuring the separation of necessary, cross-paired fluids, such as those given as examples, as is more fully indicated in the example illustrated in FIG. 8.

In this preferred embodiment of the invention 10, the receptacle 14 and its placement will help to assure that fluids that should not be intermixed or used at an inappropriate time are not crossmixed, as well as the provision or adaptation of the invention 10 to receiving one of two different sized containers 16*x*, and not 16*y*, as indicated.

The receptacle 14 can also be provided in preferred embodiments of the invention in cylinder-like, rectangular-like, square like, triangular-like, parallelogram-like, trapezoid-like and elliptical configurations, sized in appropriate dimensions to accept the smaller fluid bag 16*x* and reject or not reasonably accept the larger fluid bag 16*y* as earlier described.

Additionally, in these preferred embodiments of the present invention, the bottom or support end of the receptacle 14 provided with a U-shaped slot 20, which can also be otherwise shaped or apertured, as is illustrated by example in FIGS. 2, B, 6, 7, and 8, which continues substantially conterminously concurrently up from the bottom end, through the length of the receptacle 14 to its top portion, as illustrated in FIGS. 1, 2, 3, and 5.

The invention 10 in a preferred embodiment thereof is provided with a guide means or system 22 for guiding or tracking the appropriate, proper fluid supply line 26 from the plasmapheresis or blood unit 18, to the slotted area 20 so that it can properly be connected to the fluid container 16*x* for supply of the desired fluid in the blood collection process carried on by the unit 18, as illustrated in FIG. 8.

Additionally, the invention 10 is provided with means for attaching the receptacle 14 to the plasmapheresis or blood unit 18. Preferably this means will consist of an attachable and detachable bonded resin or glue which can secure one of the sides of the receptacle 14 to the unit 18. This means can also include the utilization of a glue-like, peelable strip to secure the left or right sides of the receptacle, 14*a* or 14*b* respectively; or a special base attachment to any of the appropriate or available sides to mount the receptacle 14 to the unit 18.

In another preferred embodiment of the invention 10, a cross-spike prevention assembly 30 is provided within the concepts of the present invention.

This preferred embodiment is illustrated in FIGS. 9, 10, 11, 12, 13, 14, 15, 16, 17, 18 and 19. A cross-spike prevention assembly 30 is utilized as an improved means and process of assuring separation of an anticoagulant fluid 34 from a saline solution 38 in the process and operation of plasmapheresis apparatus 42; a device specifically functioning to accept blood from a donor, separate out and store the plasma component of the blood collected, and return fluid in the form of saline or other acceptable or like fluid or solution to the donor's body as a part of an infusion process of the apparatus 42.

A cross-spike receptacle component 44, as was earlier described with regard to the receptacle member 14, and that embodiment of the invention 10, is dimensioned to spatially receive a container of anticoagulant fluid 34, but so that it will not receive a container of saline solution 38, in a process or procedure of utilizing the invention where each respective container is provided so that the container for anticoagulant 34 is substantially smaller than the container housing saline solution 38.

The receptacle component 46 is installed on the plasmapheresis apparatus 42 to further facilitate and assure fluid seperation by positioning the receptacle 46 for attachment to the apparatus 42 so that the fluid connection line specifically designed in the apparatus to connect to the supply of saline solution 38 will not be able to reach or connect to the positioned attachment of the receptacle component 44.

The receptacle component 44 is preferably constructed from any of a number of partially to substantially transparent, moldable, resilient materials, including, but not limited to, various plastics, resin or fiber-glass composite materials, or other such materials or different substances.

Figure 18:
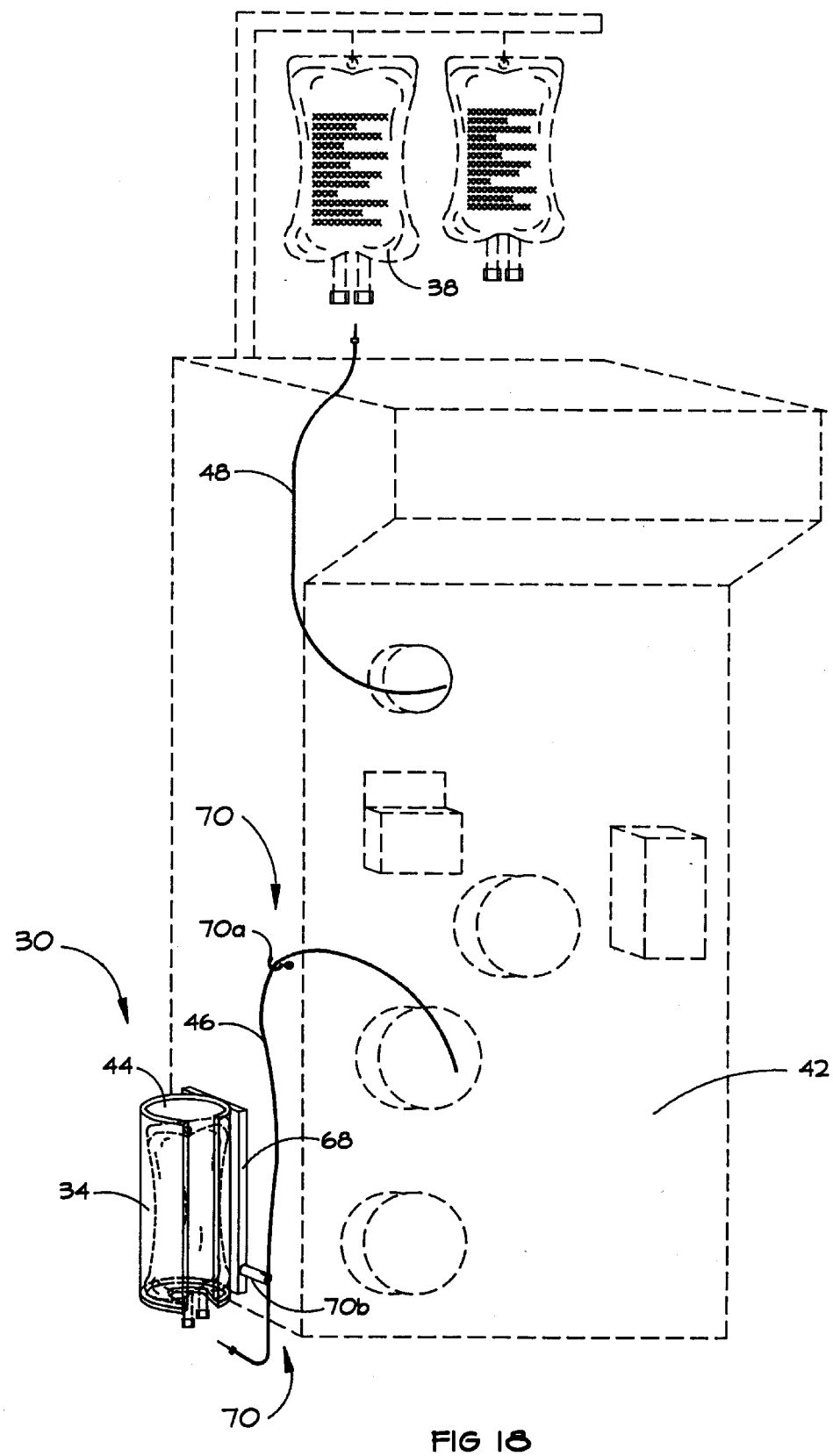
FIG. 18 is a side perspective view illustrating a preferred embodiment of the present invention, illustrating the invention in an installed condition and the spatial relationship and positioning so that only the preferred fluid communication can reach the receptacle of the invention.
Figure 19:
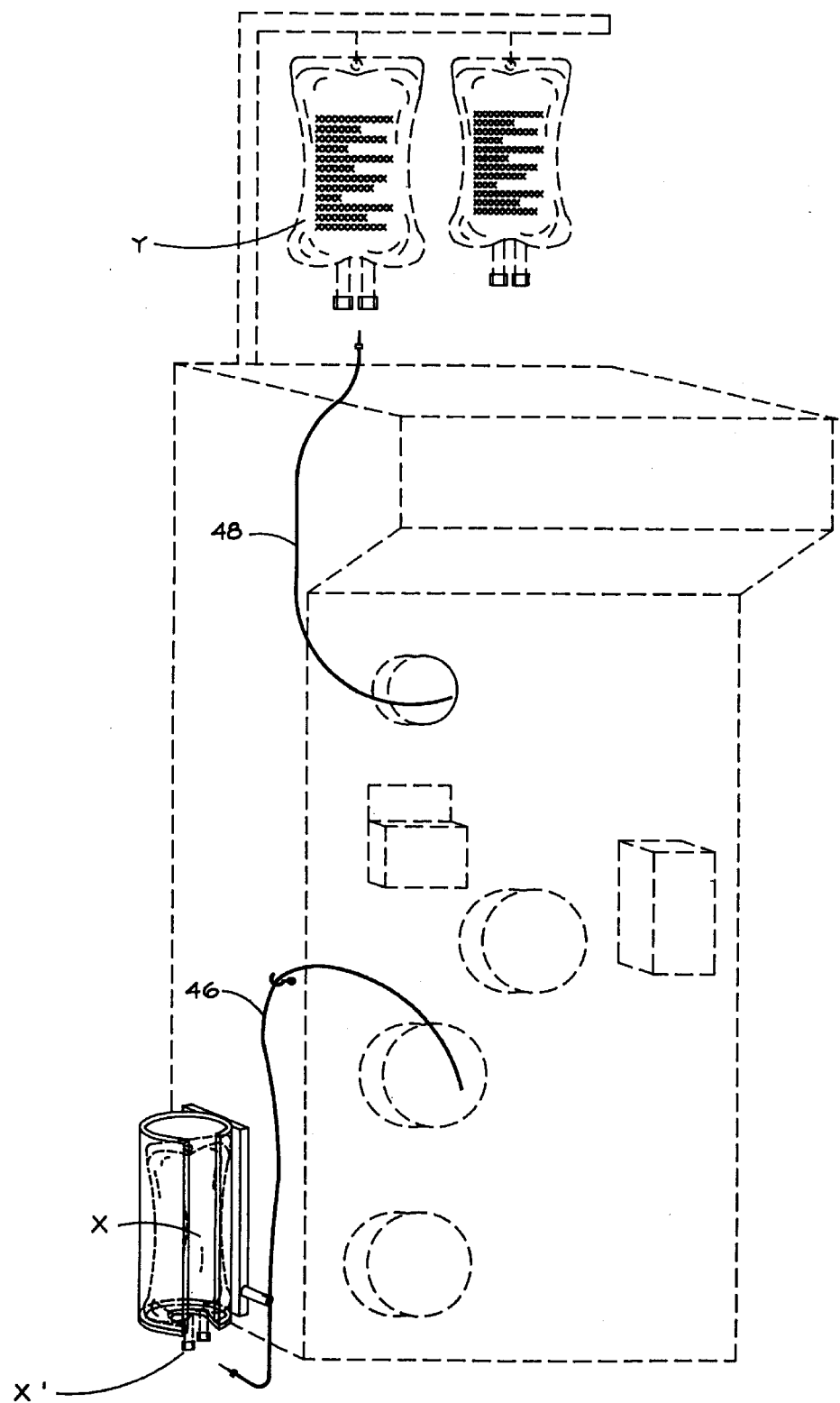
FIG. 19 is a perspective view similar to FIG. 18 illustrating the invention installed on a plasmapherisis maching (indicated in phantom lines), emphasizing the spatial relationship of the fluid line system as augmented in the proces of the present invention.

In accordance with the concepts of the invention, the dimensioning and positioning characteristics of the present invention are illustrated in FIGS. 18 and 19. A anticoagulant fluid supply line 46 is illustrated in FIG. 18 extending down to the general area of connection to the receptacle component 44 housing the anticoagulant fluid 34, shown housed therein in phantom. Also illustrated in FIG. 18 is the positional allignment of the saline solution communication line 48, indicating its ability to reach the container holding saline solution 38, but its relative substantial inability to reach the installed cross-spike receptacle component 44.

Figure 11:
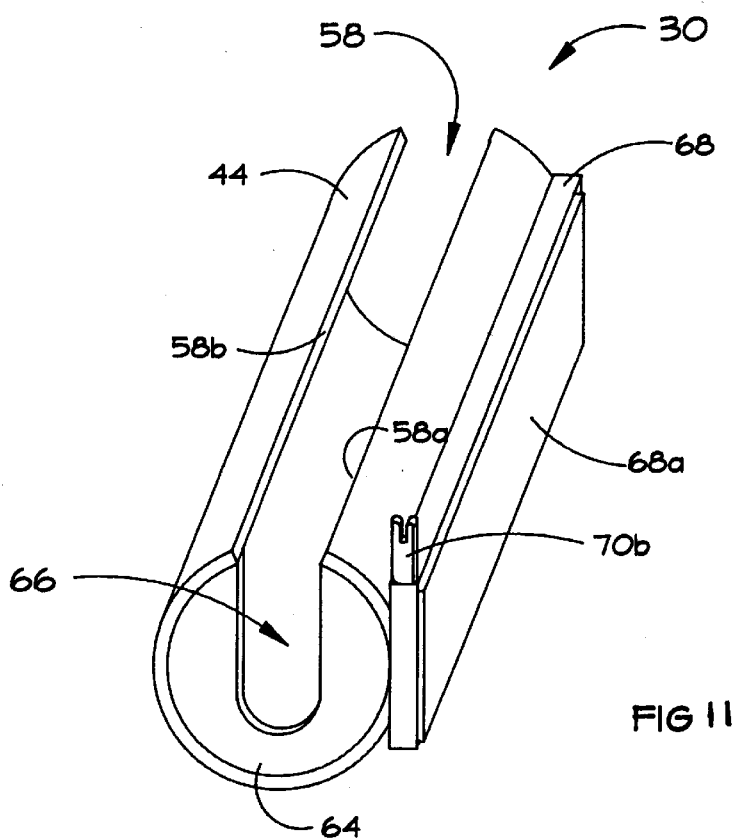
FIG. 11 is a bottom perspective view of the preferred embodiment illustrated in FIG. 9.
Figure 12:
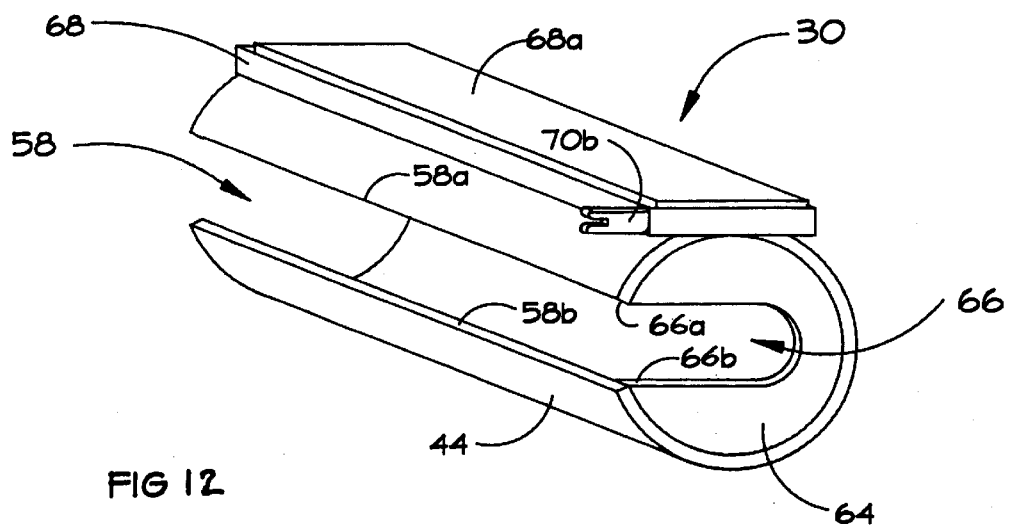
FIG. 12 is a side-front perspective view of the present invention, as illustrated in FIGS. 9 through 11.
Figure 16:
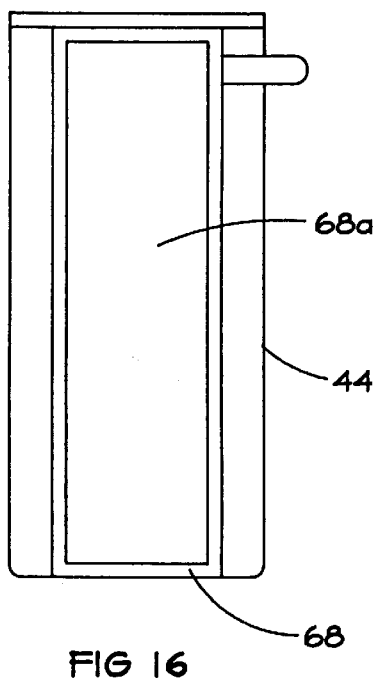
FIG. 16 is a back view of an embodiment of the invention.
Figure 14:
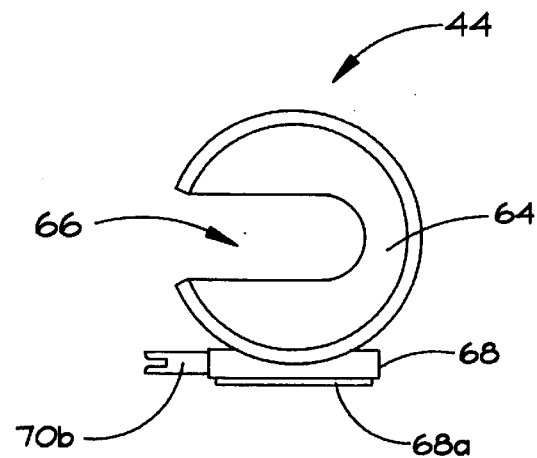
FIG. 14 is a top view of an embodiment of the present invention.
Figure 15:
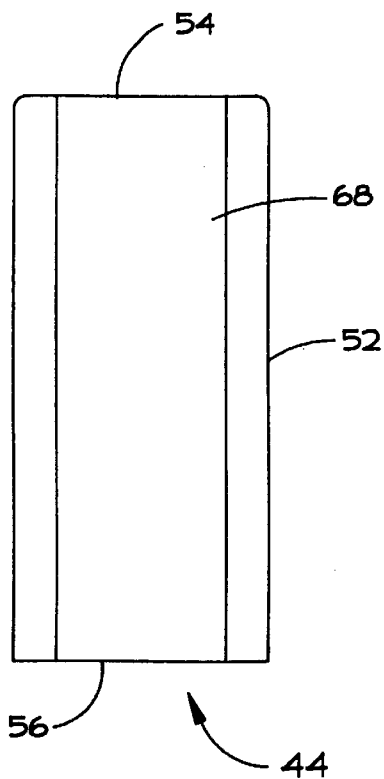
FIG. 15 is a side view of the cylinder wall of a preferred embodiment of the invention.
Figure 13:
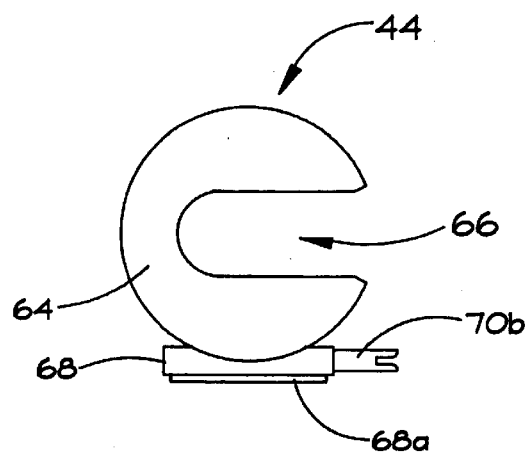
FIG. 13 is a bottom view of a preferred embodiment of the present invention.

In a preferred embodiment of the assembly 30, the cross-spike receptacle component 44 is provided in a cylindrically oriented configuration. Accordingly, the receptacle component 44 is provided in a subassembly having a rounded circumferential-wall 52 provided with two respective open ends 54 and 56 at each end of the wall 52. The wall 52 is also provided with a slotted, channeled area 58 which has perimeters, 58a and 58b respectively, which are substantially parallel to one another, and extend the length of the wall, as illustrated in FIGS. 11 and 12.

In this embodiment illustrated in FIGS. 11 and 12, and FIGS. 13 through 19, the assembly 30 is further provided with a bag support member 64. The support member 64 has a perimeter conterminous with the dimensions of the second end 56 of the wall 52 and is attached to or integrally alligned with the end 56 of the wall 52. The support member 64 is provided with a U-shaped slot 66 whose top end portions 66a and 66b are integral or conterminal with the parallel perimeters 58a and 58b of the wall 52.

Figure 17:
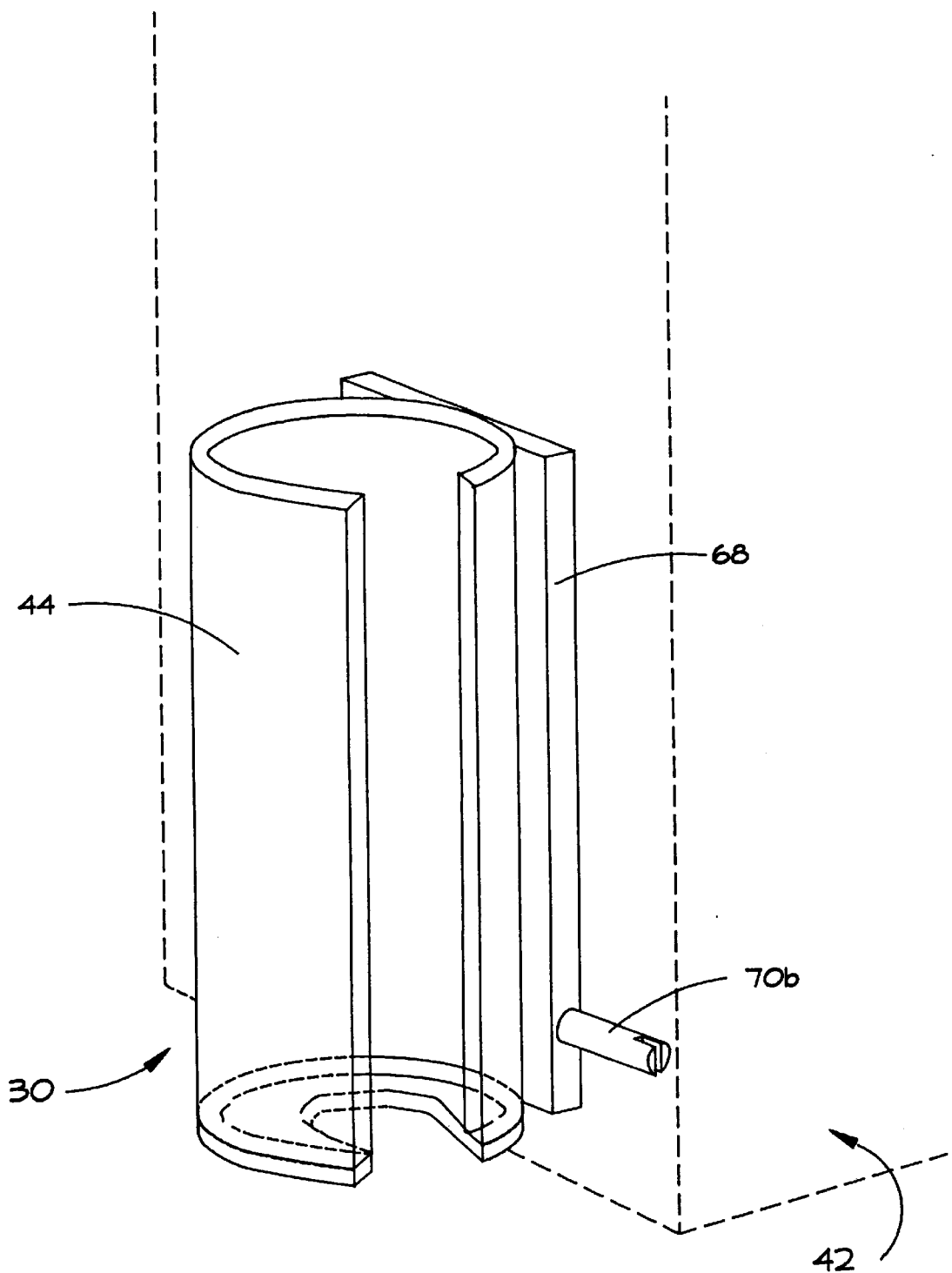
FIG. 17 is a front-side perspective view of a preferred embodiment of the present invention, illustrating the invention installed or attached onto a plasmapheresis apparatus (indicated in phantom lines).

The assembly 30 is also provided with a mount base sub-assembly 68 which is substantially rectangular in configuration, but which can be provided in many different configurations. In a preferred embodiment, the mount base 68 is provided with an attachment means or strip 68a, for attaching the, assembly 30 to the apparatus 42, as illustrated in FIGS. 10, 11, 12, 13 and 14. The mount base is preferably attached to the wall 52 of the recepticle component 44 so that the slotted area 58 of the wall 52 will face substantially, for the most part, in a frontward direction when installed on the plasmapheresis apparatus 42, as illustrated in FIG. 17, 18 and 19.

The assembly 30 is also provided with guide means 70 for guiding and tracking the anticoagulant fluid supply line 46 from the plasmapheresis apparatus 42 to the slot 66 of the bag support member 64, once the assembly 30 is positionally alligned and attached to the apparatus 42, as illustrated in FIGS. 18 and 19. In a preferred embodiment, the guide means 70 of the assembly 30 consists of a first guide member 70a mounted on the side or other functional position on the plasmapheresis apparatus 42 and a second guide member 70b mounted on the base subassembly 68, as illustrated in FIGS. 17, 18 and 19. The members 70a and 70b cooperate to guide the anticoagulant fluid supply line 46 from the apparatus 42 to connection with the anticoagulant fluid 34, when properly installed, housed in the receptacle component, and to otherwise exaggerate the fact that the saline solution 48 cannot functionally reach the installed U-shaped slot 66, bag support member 64 and anticoagulant fluid 34 so housed.

As illustrated in FIGS. 18 and 19, in this preferred embodiment, the cross-spike prevention assembly 30 can be properly installed by detachable mounting of the mount base 68 on the left bottom side of the plasmapheresis apparatus 42, with which it is designed to cooperatively work, to prevent cross-spiking of potentially dangerous fluids.

By virtue of the manner in which the invention 10, and its preferred embodiments including the assembly 30, function; part and parcel of the concepts of the invention are set forth in a process for cross-spike prevention, facilitated by the structure and function of the present invention.

Accordingly, a preferred embodiment of the invention includes the process for assuring separation of anticoagulant or other such fluids from saline solution or other such fluids utilized in the process and operation of a blood collection or plasmapheresis apparatus, when the apparatus or inherent process incorporated therein requires the separation of one type of fluid from the use or supply of a second type or kind of fluid, as earlier described herein. The process of the present invention includes providing an anticoagulant-type fluid in a fluid bag which can be identified as fluid bag x, and a saline or like type of solution or fluid placed in a container identified as bag y, or in another distinguishing manner, where the fluid bag x is provided in a substantially smaller volume than fluid bag y, and fluid bag x is utilized in the collection phase of a plasmapheresis or other blood collection device to maintain blood and plasma collected or stored in the device in a substantially uncoagulated, fluid state or condition, and fluid bag y is utilized in an infusion phase of the device to replenish fluid in a respective blood or plasma donor.

The process further includes dimensioning the receptacle 14, 44, so that it will slideably and slotably receive the smaller fluid bag x, and exclude or reject, or not receive, the larger fluid bag y should installation and housing in the receptacle 14, 44, be attempted. The receptacle 14, 44, in this stage of the process is also dimensioned, cut and/or molded, as the term used herein includes, as a part of its meaning, so that when fluid bag x is received and installed in the receptacle, a supply channel at the bottom of the fluid bag can extend through the bottom of the receptacle 14, 44, to receive the fluid supply line 26, 46, from the plasmapheresis or blood collection device 18, 42.

The process of the present invention further includes distancing and coupling the receptacle 14, 30 and/or 44, to a position, spatially and positionally, on the plasmapheresis or like device 18, 42, so that the receptacle is installed positionally or spatially relevant to the anticoagulant or like fluid supply line 26, 46, at a distance reasonably and/or substantially greater than the length of the saline or like fluid supply line 48 utilized by the plasmapheresis unit 18, 42.

The process also further includes guiding the anticoagulant fluid line 26, 46, to the coupled and attached receptacle 14, 30, 44; and slideably or slotably installing a fluid bag x into the receptacle 14, 30, for use in the collection phase of the plasmapheresis device 18, 42, so that the supply channel x' of the fluid bag x, containing anticoagulent fluid, extends through the bottom of the receptacle and is available to receive and be coupled to the anticoagulant or like fluid supply line 26, 46, from the plasmapheresis unit 18, 42, as illustrated in FIG. 19.

The process then, also, includes connecting and coupling the guided anticoagulant or like fluid supply line 26, 46, to the supply channel x' of the fluid bag x so that this fluid can be used in the collection phase of the plasmapheresis device 18, 42.

In that part of the present process of the invention which includes distancing and coupling the receptacle 14, 30 and/or 44, to a position for installation on a plasmapheresis unit or apparatus for use in accordance with the concepts of the invention, it was earlier indicated in the specification that any number of attaching or coupling means can be employed to attach the receptacle element or member to the plasmapheresis unit. In an example of a preferred embodiment of the invention, FIGS. 7B, 8, 9, 10 and 11, illustrate an adhesive strip 68a being utilized on and/ or as a part thereof of the mount base subassembly 68 of the cross-spike prevention assembly in a preferred embodiment 30. It will be understood that a number of different means of attachment can be used on or as a part of the mount base subassembly 68, or that the respective preferred embodiments of the present invention's receptacle 14 and 44 can be mounted direcly on the the plasmapheresis unit or blood collection unit, as is illustrated in FIG. 6 of the present drawings herein.

While the present invention has been described in connection with the particular embodiments thereof, it will be understood that many changes and modifications of this invention may be made by those skilled in the art without departing from the true spirit, concepts and scope thereof.

Accordingly, the appended claims are intended to cover all such changes and modifications as falling within the true spirit and scope of the present invention. The reader is requested to determine the scope of the invention by the appended claims and their legal equivalents, and not by the examples which have been given.

Having described my invention, I claim:

1. A process for assuring separation of at least two distinct and different fluids comprising a first fluid and a second fluid, utilized in a process and operation of a blood plasma apparatus, having respective and different fluid supply lines in communication with each of said fluids for communicating and transporting each of the respective fluids from a respective first supply container and a respective second supply container, to the apparatus, when a blood plasma process requires separation of the first fluid and the second fluid, said process comprising:

providing each of the supply containers such that the first supply container is dimensioned smaller in operational, spatial size than the second supply container;

dimensioning a receptacle such that it will installably and operationally receive one of the supply containers and not installably and operationally receive the other supply container; and positioning and supporting the receptacle in a position relative to the blood plasma apparatus such that the receptacle is installed adjacent and proximal to an operational length of one of the fluid supply lines from the blood plasma apparatus, at a distance different and greater than an operational length of the other fluid supply line of the blood plasma apparatus.

2. A process for separating a plasmapheresis fluid from a replacement fluid utilized during the operation of a blood plasma collection apparatus which utilizes, at least, a first fluid bag and a second fluid bag, each having a separate respective fluid communication line connected thereto, to directly and separately supply a plasmapheresis fluid and a replacement fluid, respectively, said process comprising:

dimensioning each of said fluid bags such that the first fluid bag is substantially smaller in volume and spatial size than the second fluid bag;

molding a receptacle such that it defines an installation area dimensioned such that it will receive the first fluid bag and operationally exclude the second fluid bag;

positioning the receptacle adjacent to the blood plasma collection apparatus, such that the first fluid bag connected to its respective communication line of the collection apparatus will extend to and installably be supported by the receptacle and the second fluid bag connected to its respective communication line of the apparatus will not extend to and installably be supported by the receptacle, as then positioned; and spatially positioning the first fluid bag such that it is in installed position in relation to the receptacle for use with the plasma collection apparatus.

3. The process of claim 2, wherein the first fluid bag is utilized to supply an anticoagulent fluid and the second fluid bag is utilized to supply a saline solution.

4. The process of claim 2, wherein prior to said spacially positioning step the process further comprises: guiding the respective fluid communication line from the apparatus to the first fluid bag, toward and adjacent to the receptacle such that it may be attached to the first fluid bag when it is installed on the receptacle.

5. An improved process for assuring separation of an anticoagulent fluid from a saline solution fluid utilized, and requiring respective segregation, in the operation of a plasmapheresis apparatus having a anticoagulent fluid line and a saline solution fluid line, each differentially attached thereto, for communicating and separately transporting each of the respective fluids from a individual respective anticoagulent supply container and a individual respective saline solution supply container, each of which respectively houses the fluids, to the plasmapheresis apparatus, said process comprising:

dimensioning the anticoagulent supply container such that it is smaller in its operational, outer dimensional configuration than that of the saline solution supply container;

fabricating a receptacle such that it dimensionally defines a hollow installation area that will operationally accept the anticoagulent supply container and operationally not accept the saline solution supply container;

operationally installing the anticoagulent supply container into the installation area of the receptacle;

distancing and supportably positioning the receptacle relative to each of the respective fluid lines of the plasmapheresis apparatus such that the anticoagulent fluid line will operationally extend and connect to the receptacle and the installed anticoagulent supply container.

6. The process of claim 5, wherein said receptacle is constructed from partially to substantially transparent, moldably resilient material.

7. The process of claim 5, wherein the process includes the additional step of providing and securely positioning support means for housing the saline solution supply container proximal and adjacent to an operational distance of the saline solution fluid line of the plasmapheresis apparatus, such that the saline solution fluid line will operationally extend and connect to the support means and the anticoagulent fluid line will not so extend and connect to the support means.

8. The process of claim 7, wherein the hollow installation area is cylindrical in configuration.

9. The process of claim 7, wherein the hollow installation area is planar in configuration.

10. An improved process for assuring separation of at least two fluids utilized in a process and operation of a plasmapheresis apparatus, when a plasmapheresis process requires separate respective fluid supply lines to and separation of a fluid x and a fluid y, where at least one of the fluids is utilized to maintain collected blood and plasma present in a plasmapheresis apparatus in a substantially noncoagulated and fluid and healthy state during a collection phase, and the other fluid is utilized in an infusion phase of the plasmapheresis process to return or replenish a fluid in a respective donor, said process comprising:

provicing a first fluid in a fluid bag x and a second fluid in a fluid bag y, where the fluid bag x is provided having a smaller volume capacity than fluid bag y;

dimensioning a receptacle such that it will installably and operationally receive one of the fluid bags and not installably and operationally receive the other fluid bag when such installation is attempted; and distancing and coupling the receptacle to a position in reference to the plasmapheresis apparatus such that the receptacle is installed adjacent and proximal to an operational length of one of the fluid supply lines from the plasmapheresis apparatus, at a distance substantially different than an operational length of the other fluid supply line of the plasmapheresis apparatus.

11. The improved process of claim 10, wherein the first fluid provided in the fluid bag x is a anticoagulant fluid and the second fluid provided in the fluid bag y is a saline solution fluid.

12. The improved process of claim 10, wherein the process further comprises:

guiding the anticoagulant fluid supply line of a plasmapheresis device to a spatial area outboard of the coupled receptacle;

installing the fluid bag x on the receptacle for utilization in the collection phase of the plasmapheresis device, such that a supply channel of the fluid bag x extends outboard of the receptacle and is available to receive and be coupled to the anticoagulant fluid supply line from the plasmapheresis apparatus;

connecting and coupling the guided anticoagulant fluid supply line to a supply channel of fluid bag x such that the anticoagulant fluid can be utilized in the collection phase of the plasmapheresis apparatus; and operatively attaching the saline solution fluid supply line to a supply channel of fluid bag y such that the saline solution fluid can be utilized in the infusion phase of the plasmapheresis apparatus.

13. The improved process of claim 11, wherein the saline solution fluid supply line is provided on the plasmapheresis apparatus having a shorter operational length than an operational length of the anticoagulant fluid supply line on the plasmapheresis apparatus.

* * * * *